United States Patent [19]

Huckins et al.

[11] Patent Number: 5,395,426
[45] Date of Patent: Mar. 7, 1995

[54] DEVICE FOR THE REMOVAL AND CONCENTRATION OF ORGANIC COMPOUNDS FROM THE ATMOSPHERE

[75] Inventors: James N. Huckins; Jimmie D. Petty; James A. Zajicek; Virginia L. Gibson, all of Columbia, Mo.

[73] Assignee: The United States of America as represented by the Secretary of the Interior, Washington, D.C.

[21] Appl. No.: 87,374

[22] Filed: Jul. 8, 1993

[51] Int. Cl.$^6$ ............................................. B01D 53/22
[52] U.S. Cl. ............................................. 95/44; 95/50; 96/5; 96/8; 96/12
[58] Field of Search ............... 95/44, 45, 50; 96/5, 96/7, 8, 10–14

[56] References Cited

U.S. PATENT DOCUMENTS

| | | | |
|---|---|---|---|
| 3,335,545 | 8/1967 | Robb et al. | 95/44 |
| 3,447,286 | 6/1969 | Dounoucos | 95/44 |
| 3,751,879 | 8/1973 | Allington | 96/5 |
| 3,911,080 | 10/1975 | Mehl et al. | 95/45 X |
| 4,174,374 | 11/1979 | Matson | 95/44 X |
| 4,269,804 | 5/1981 | Kring | 96/10 X |
| 4,710,205 | 12/1987 | Deetz et al. | 96/5 |
| 4,750,918 | 6/1988 | Sirkar | 96/5 X |
| 4,900,448 | 2/1990 | Bonne et al. | 96/44 |
| 4,915,838 | 4/1990 | Bonne et al. | 96/8 X |
| 4,942,135 | 7/1990 | Zaromb | 95/45 X |
| 5,013,436 | 5/1991 | Lee et al. | 96/10 X |
| 5,091,080 | 2/1992 | van Eikeren et al. | 96/10 X |
| 5,100,555 | 3/1992 | Matson | 95/44 |
| 5,104,425 | 4/1992 | Rao et al. | 95/50 X |
| 5,106,579 | 4/1992 | Fukazawa et al. | 96/10 X |

FOREIGN PATENT DOCUMENTS

0458598  11/1991  European Pat. Off. ............... 95/44

Primary Examiner—Robert Spitzer
Attorney, Agent, or Firm—E. Philip Koltos

[57] ABSTRACT

A device and method for removing, concentrating and analyzing airborne organic compounds. The device includes a nonporous membrane which contains a collection media. The liquid collection media typically includes a component which has a molecular weight that is too large to pass through transport corridors in the nonporous membrane and a component which has a molecular weight which is sufficiently small enough to pass through the transport corridors in the nonporous membrane and thereby forming a thin film on the exterior surface of the device. The collection media can consist of only components too large to pass through the membrane transport corridors. Organic contaminants are trapped in the thin film on the exterior surface of the device or the membrane and transported by concentration gradient diffusion forces into the bulk of the collection media within the nonporous membrane.

18 Claims, 3 Drawing Sheets

DEVICE FOR THE REMOVAL AND CONCENTRATION OF ORGANIC COMPOUNDS FROM THE ATMOSPHERE

TECHNICAL FIELD

The present invention relates to the collection and analysis of airborne organic contaminants. More particularly, the present invention relates to devices and methods for the removal and concentration of organic compounds from the atmosphere.

BACKGROUND ART

A variety of techniques have been employed to measure deposition of atmospheric contaminants (see for example: Methods of Air Sampling and Analysis, 3rd ed., J. P. Lodge, Jr. Ed., 1989, Lewis Publishers, Inc. Chelsea, Mich.). Known techniques include the use of devices which incorporate glycerol-coated plates or pans, Teflon sheets, containers of water, polyurethane foam plugs, carbon or other adsorbent traps and glass fiber or paper filters. Such devices suffer from the adverse consequences of instability, complexity, and mechanical operation. For example, samplers having open containers of liquids (so called impingers) suffer from evaporative losses, microbial contamination, and the effects of changing weather conditions.

Air filtration based samplers are subject to variable filtration rates as particulate matter is accumulated on the surface or deposited within the filter media. The particulate matter acts as an additional filtration media with the potential of reducing flow rates of air through the system. Also, the particulate matter often adsorbs vapor phase organic compounds at a rate significantly greater than the original inert filter thus, resulting in imprecise or inaccurate residue values.

Mechanical or active sampling devices require power to operate pumps, vortex tubes, precipitators, etc. In addition, in most instances such sampling devices must be calibrated for each set of analyses. All such configurations are subject to various failures.

Passive samplers based on air diffusion are often subject to errors caused by variations in air face velocity. Trapping media suitable for use in diffusion samplers are confined primarily to adsorptive solids. Because commonly used diffusion membranes are porous to water vapor, the solid adsorbents are susceptible to the deleterious effects of humidity.

Laboratories involved in the analysis of trace quantities of organic pollutants, such as polychlorinated biphenyls (PCBs), must have atmospheres which are practically free of these chemicals to prevent false-positive results, i.e., reporting that a chemical was present in a sample when it actually came from the laboratory environment.

To ensure that airborne contamination of samples is not a problem in laboratories, a simple and effective way to monitor air at very low levels for targeted analytes (organics) is needed. Unfortunately, current methods usually require complex sampling apparatus such as calibrated pumps and are usually not integrative over sufficient time intervals to pick up ultra-trace level contaminants and episodic releases.

DISCLOSURE OF THE INVENTION

It is accordingly an object of the present invention to provide a device for removing and concentrating organic compounds from the atmosphere.

Another object of the present invention is to provide a passive device for removing and concentrating organic compounds from the atmosphere.

A further object of the present invention is to provide a device for removing and concentrating organic compounds from the atmosphere which mimics respiratory uptake of organic compounds in the lungs.

It is a further object of the present invention to provide a device which removes or reduces the concentration of organic compounds in an environment.

A still further object of the present invention is to provide a method of removing and concentrating organic compounds from the atmosphere.

A still further object of the present invention is to provide a method of removing or reducing the concentration of organic compounds in an environment.

According to these and further objects of the present invention which will become apparent as the description thereof proceeds, the present invention provides a device for collecting organic compounds from an atmosphere which includes:

an envelope made from a nonporous membrane which includes an inner space, an exterior surface, and membrane transport corridors which provide pathways for exchange between the inner space and the exterior surface; and an organic compound collection media within the inner space, whereby organic compounds are absorbed by the nonporous membrane and are transported through the membrane transport corridors into the inner space of the envelope.

The present invention further provides for a method for collecting organic compounds from an atmosphere which involves:

providing an envelope made from a nonporous membrane which includes an inner space, an exterior surface, and membrane transport corridors that communicate between the inner space and the exterior surface;

providing an organic compound collection media within the inner space; and exposing the envelope to an atmosphere which contains organic compounds, whereby organic compounds are absorbed by the nonporous membrane and are transported through the membrane transport corridors into the organic collection media in the inner space of the envelope.

According to more preferred embodiments of the present invention, the organic compound collection media includes a first component which has a molecular weight which is too large to pass through the membrane transport corridors and a second compound which is sufficiently small so as to pass through the membrane transport corridors, and thereby form a thin film of the second component on the exterior surface of the envelope.

BRIEF DESCRIPTION OF DRAWINGS

The invention will be described with reference to the attached drawings which are given by way of nonlimiting examples only in which.

BEST MODE FOR CARRYING OUT THE INVENTION

The present invention is directed to a novel device for collecting organic components from the atmosphere which provides a new approach for handling several major contaminant-related problems confronting the F&WS, EPA, NIOSH, etc. For example, the device of the present invention can be used as an atmospheric contaminant monitoring tool. The device of the present invention can also be employed in the remediation of atmospheric pollutants in sick or contaminated buildings and in other large scale applications.

The device of the present invention includes a concentration media which absorbs several types of chemical and biochemical components, thus enabling the device to be used in the performance of various types of chemical and biochemical assays. For example, the toxicological significance of sequestered contaminant residues can be directly assessed, which is a major shortcoming of current analytical methods used by government agencies.

The present invention has been found to be particularly useful for monitoring the average exposure of humans and other living things to airborne organic vapors while at the same time sequestering enough mass of these contaminants for toxicological assessments. In addition, the device of the present invention can be used to reduce airborne toxic chemical concentrations in buildings or other defined areas.

Since the present invention is simple to operate, it can be readily used by regulators, managers, and investigators for measuring the amounts of organic compounds in indoor and outdoor settings, for predicting the adverse effects of such contaminants, and for remediating unacceptably high concentrations of airborne chemicals.

The device of the present invention was designed to function in such a manner so as to mimic respiratory uptake of airborne contaminants. Respiratory uptake generally involves active transport to a biomembrane surface (breathing), movement through the exterior mucosal layer and the membrane, and export away from the membrane's inner surface (circulation of blood) to lipid-containing tissues. Although contaminant uptake by respiration is complex, the process can be simplified to its passive elements which include diffusion of organic contaminants through thin stagnant air and liquid phase layers, the nonpolar regions of biomembranes, and finally into an organism's lipid pool. The present invention was designed to simulate most of these characteristics of the respiratory uptake process. However, the present invention does not attempt to simulate lung morphology.

The invention consists of a sealed nonporous polymeric membrane tube which contains a lipid, oil, or other lipid-like trapping media. The polymeric membrane tube can have either a layflat or turgid design and is preferably made from a material which, after a sufficient period of time, allows an ultrathin film of small sized lipids to form on the exterior membrane surface. The polymeric membrane tube is preferably made of a thin-walled nonporous polyethylene, polypropylene, polyvinyl chloride, silicone, or the like. Alternatively, a thin layer of nonporous polymer can be laminated or grafted to a thicker microporous polymer such as microporous polypropylene to increase strength and uptake (membrane) rates.

The transport corridors through nonporous polymeric membranes, are extremely small and usually limit or control the rate of contaminant uptake. These polymeric transport corridors are generally less than 10 angstroms, and consist of transient cavities usually not much larger than a single molecule of an organic contaminant. Because of the relatively small size (less than 550 mw) of most airborne contaminant molecules, they can move through the transport corridors in the device's membrane and into the enclosed lipid by a solution-diffusion mechanism. On the other hand, most of the lipids or lipid-like organics, used for trapping media inside the device, are too large (greater than 600 mw) to readily permeate out through the nonporous membrane. These large molecular weight lipids (e.g., triglycerides) remain inside the sealed nonporous membrane tube and the high affinity of many organic contaminants for this type of lipid provides the driving force for the contaminant uptake process.

The smaller components (less than 550 mw) of the device's enclosed lipid mixtures permeate through the nonporous membrane forming an ultrathin film of surficial lipid on the exterior surface of the membrane. The vapor pressure of these lower molecular weight constituents has been found to be quite low, preventing significant pervaporative losses. The surficial lipid film acts as a preconcentration media for organic vapors such as PCBs. The time required for the first few molecules of low molecular weight lipid components to reach the membrane's exterior surface is generally less than 8 hours (18° C., low density polyethylene, less than 100 $\mu$m thick). However, the mass of the ultrathin exterior film will typically increase over time until an ultimate amount is reached which is dependent on the percentages of low molecular weight constituents present in the lipid used in the device.

The low resistance to organic vapor transfer through the exterior lipid film interface and its high surface area, permit rapid uptake of airborne contaminant residues. As this ultrathin exterior lipid phase rapidly concentrates airborne organic vapors, a concentration gradient is created across the membrane, providing some of the driving force for the flux of organic analytes through the membrane into the bulk lipid trapping media. Ideally, the affinity of the exterior ultrathin lipid phase for airborne organics should be no greater than that of the polyethylene membrane and less than the large molecular weight lipid enclosed in the membrane tube.

Figure 1:
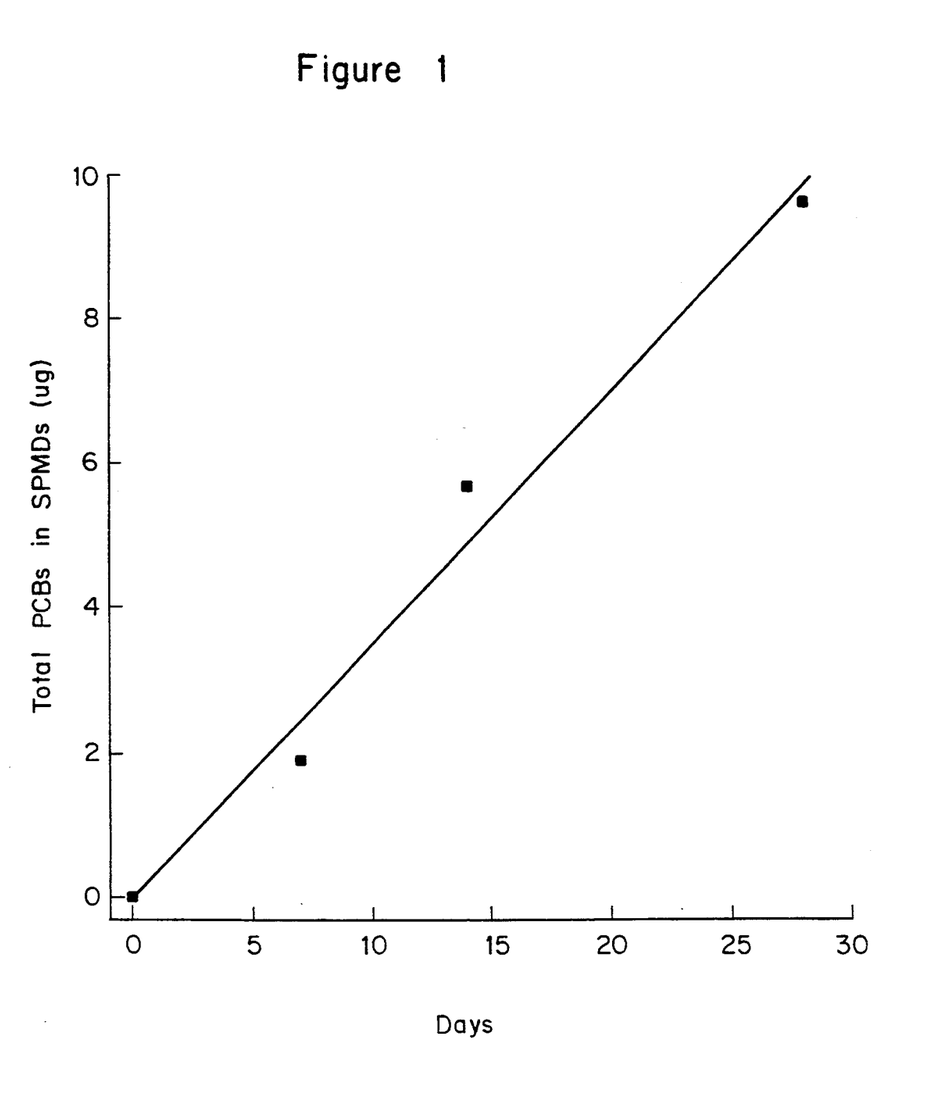
FIG. 1 shows the passive uptake of polychlorinated biphenyls (PCB's) from air over a twenty-eight day exposure period.

The major driving force for contaminant uptake and the concentrating power of the device, when it is in contact with ambient air containing organic compounds, is due to the fact that many airborne contaminants are highly lipophilic and have only moderate vapor pressures. Because of these properties, the organic compounds readily partition from the vapor phase into lipids or lipid-like media and the nonpolar membrane of the invention, and become concentrated over time. This is seen from FIG. 1 which shows that the uptake rate of PCB's from laboratory air was essentially linear over a twenty-eight day passive exposure period. The efficiency of the device is high enough that the use of several large devices is sufficient to lower airborne contaminant concentrations in confined areas.

Figure 2:
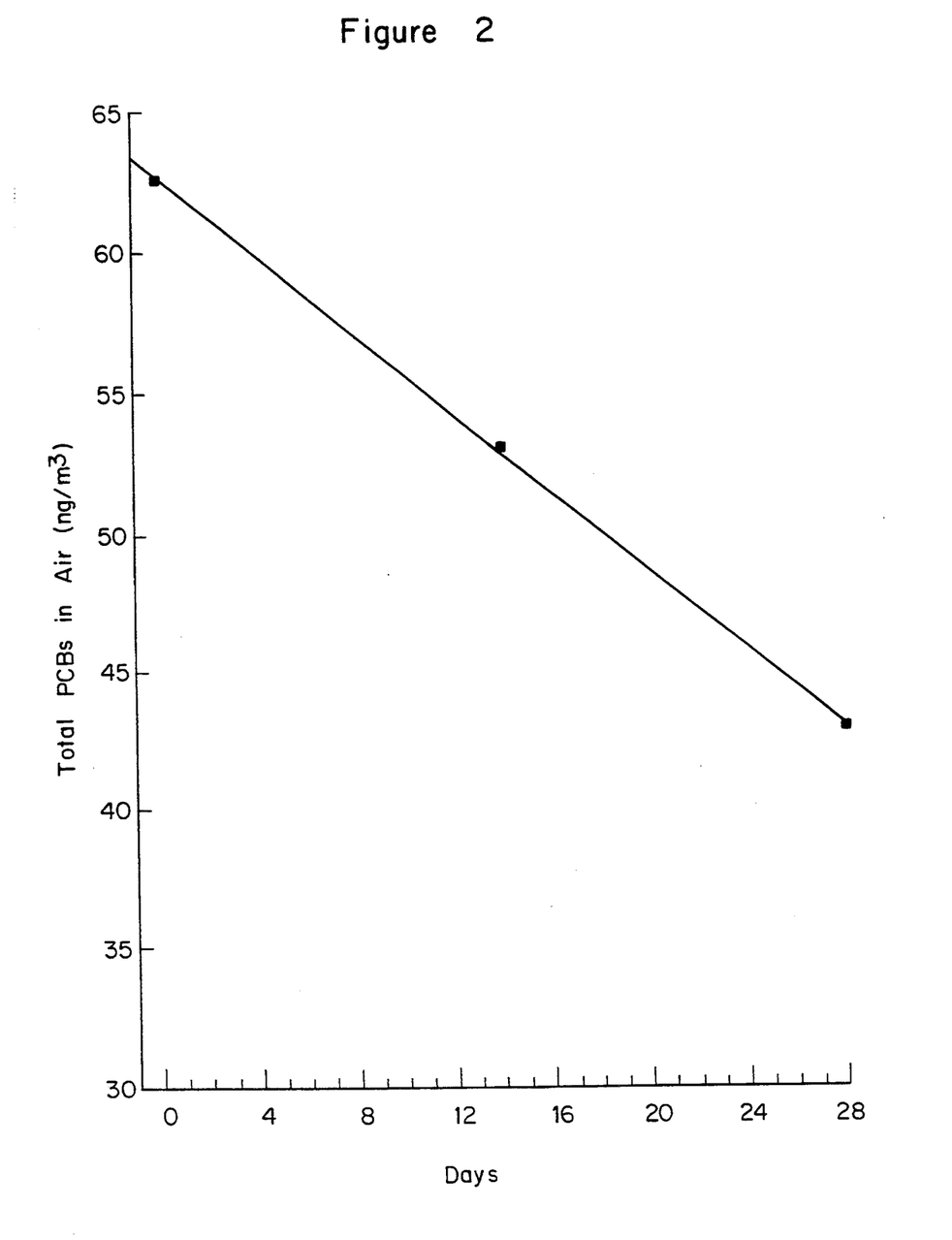
FIG. 2 shows the effect of using several of the devices of the present invention to lower polychlorinated biphenyl (PCB) concentrations in a confined area.

FIG. 2 shows the effect of using several of the devices of the present invention to lower polychlorinated biphenyl (PCB) concentrations in a confined area. A total of 9 grams of a lipid media were enclosed in the polymeric membrane devices. The volume of the area was 27 cubic meters. Concentration factors in the lipid media of more than $1 \times 10^5$ fold higher than the ambient air concentrations were demonstrated for PCBs (see FIGS. 1 and 2).

It is hypothesized that contaminants with relatively high non-dimensional Henry's constants (greater than $1 \times 10^{-2}$) will have rapid uptake rates by the present device, but relatively low equilibrium concentration factors (less than $1 \times 10^4$) in the sequestering lipid phase. It is also anticipated that as the octanol-water partition coefficients of a series of organic compounds increases, their equilibrium concentrations (during similar exposure intervals and conditions) in the enclosed lipid phase will increase proportionally. However, their uptake by the device will increase only up to a point and then plateau or slightly decrease as molecular size affects membrane permeability. This size effect does not appear to be evoked until the cross-sectional diameter of a molecule exceeds 9 angstroms, which generally does not apply to organic vapors. Then, for most analytical applications, the uptake rates of organic compounds by the device should be proportional to their ambient concentrations, which enables the use of this invention as a quantitative integrative monitor of airborne contaminants.

In the case of analytical applications, recovery and cleanup of enriched contaminants in the device of the present invention are accomplished using widely recognized standard techniques (i.e., dialysis, adsorption chromatography, size exclusion chromatography, high performance liquid chromatography, gas chromatography, and the like. Likewise, analysis of collected contaminants can be performed utilizing various standard techniques, including chromatographic detection techniques, mass spectrometry, etc.).

Figure 3:
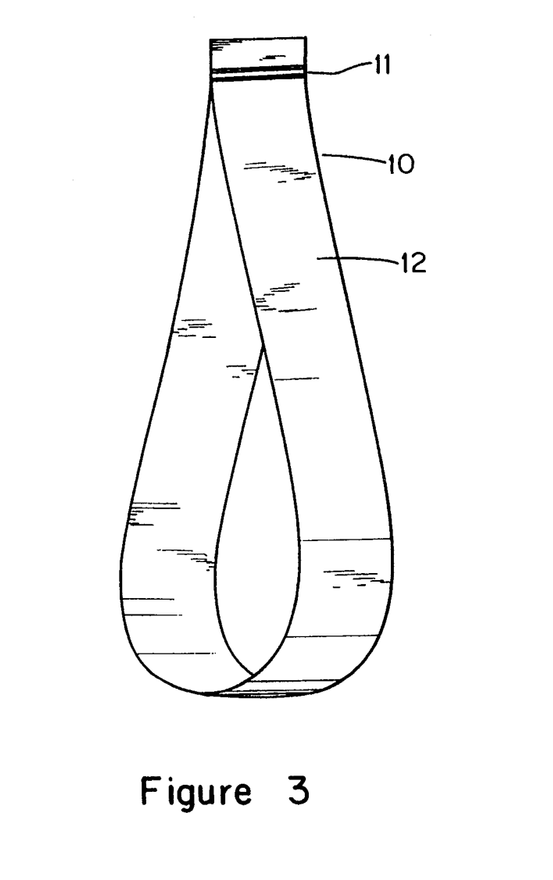
FIG. 3 is a perspective view of a device according to one embodiment of the present invention.
Figure 4:
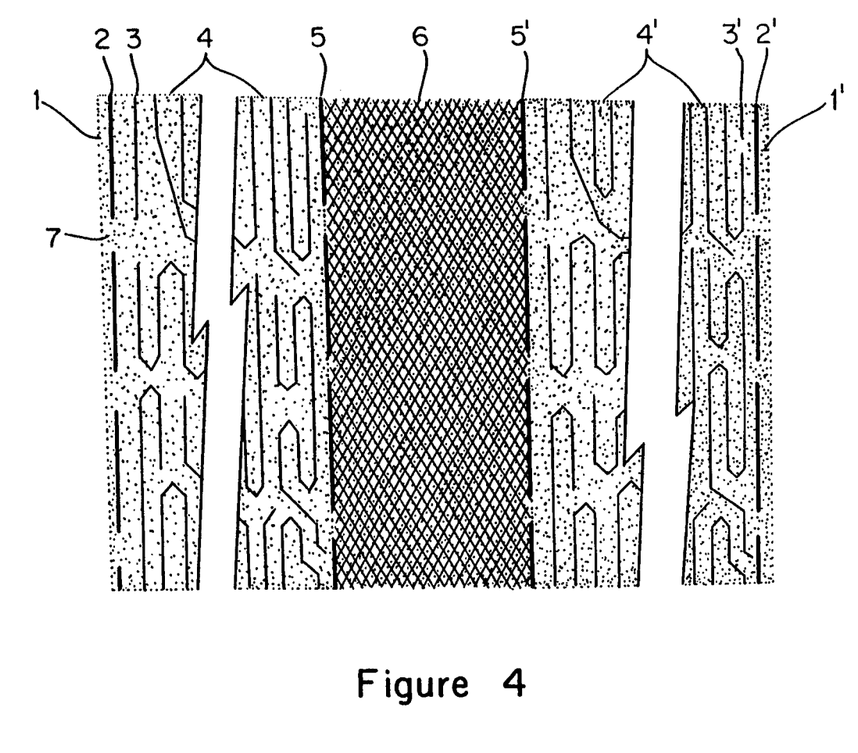
FIG. 4 is a cross sectional view of the membrane tube according to one embodiment of the present invention.

The physical configuration of the device of the present invention can be varied depending on the specific application and its scale. One embodiment of the device of the present invention is shown in FIG. 3. The device shown in FIG. 3 was designed for passively monitoring organic contaminants in the atmosphere. The ultrathin exterior lipid layer is shown in FIG. 4 but may not always be present if all lipid constituents are greater than 600 daltons molecular weight. Even without the exterior lipid layer, the device operates efficiently because of the high affinity of lipophilic organic vapors for a nonpolar membrane.

The device shown in FIG. 3 includes a membrane tube 10 which is configured as a loop. The membrane tube 10 is filled with a lipid media and the two ends of the membrane tube 10 are heat sealed at a portion 11, which is near the two ends. As discussed herein, the lipid media 12 is sandwiched as a thin film inside the membrane tube 10.

FIG. 4 is a cross sectional view of the membrane tube according to one embodiment (FIG. 3) of the present invention. As depicted in FIG. 4 the nonporous polymeric membrane 4, 4' is of a tubular configuration and includes an interior surface 5, 5' and an exterior surface 2, 2'. A high molecular size lipid media 6 is contained within the interior surfaces 5, 5' of the membrane and is prevented from passing through transport corridors 7, 7' due to the large molecular size of the lipid media 6. A low molecular weight portion of the lipid media forms an ultrathin layer 1, 1' on the exterior surface 2, 2' of the membrane by passing through transport corridors 7, 7' formed between polymer chains 3, 3' of the membrane. The transport corridors allow selective exchange between the exterior surface and the interior portion of the device.

There are a number of possible configurations of the present device and process parameters which can be used for sequestration of organic compounds from the atmosphere. For example, the size of the device alone can be an important selection criteria for a particular use. A relatively small device can be used for small scale analytical purposes. A larger device can be used in an industrial or remedial application. A number of types of nonporous synthetic polymeric films or membranes can be used to make the device, including polyethylene, polypropylene, silicone (with and without plasma treatment) and Silastic ® polyvinylchloride, chlorinated polyethylene, chlorosulphonated polyethylenes, polyimides, polyethylene vinylacetate copolymer, polyethylene terphthalate, and the like. In addition, laminates of microporous polymers with these nonporous synthetic polymeric films or membranes can also be used. A preferred membrane tested during the course of the present invention included a polyethylene membrane. Polyethylene was selected because of its low cost and applicability to nonpolar contaminants. However, each of the above polymers can also be used according to the present invention.

Relatively thin polymeric films of 0.0002 to 0.0196" (5 to 500 μm) thickness are generally better suited for both analytical and industrial or large scale configurations of the present device, because of the need to minimize transport times of contaminants through the polymer matrix. As mentioned earlier, applications requiring maximum uptake rates of airborne contaminants can be configured of extremely thin, e.g. about 1 μm, nonporous membranes which are laminated to thicker microporous membranes.

In most cases membrane transport rate is the major factor controlling the time required to reach steady state or to saturate the device. Saturation completes the uptake process and requires replacement by a fresh device if monitoring or cleanup is to be continued. In general, increasing the film thickness of the nonporous polymer to improve mechanical strength reduces membrane permeation or sequestration rates (typically in a linear manner at constant temperature and pressure) of non-electrolyte organic compounds. A membrane thickness of less than or equal to 200 μm is recommended for small scale (up to 100 mL of model lipids) analytical applications of the invention. However, applications such as the use of large volumes of fats or model lipids enclosed in polymeric films for removal of organic contaminants from various atmospheric systems may require the greater strength and durability of the upper range of film thickness, i.e. 100 to 500 μm. Also, for hydrocarbon polymers such as polyethylene or polypropylene, properties of low density, low crystallinity (commercial polyethylene generally ranges from 60 to 95% crystallinity), and low chain orientation are generally desirable because these properties maximize contaminant transport rates through film matrices, which controls the rate of contaminant uptake or removal from the atmosphere. These characteristics are usually representative of low density polyethylene films used to make commercial plastic bags.

The surface-area-to-volume ratios (ratio of surface area of polymer film or membrane to membrane enclosed lipid media) used for this invention can vary greatly depending on the nature of the particular application for the device. The range of preferred surface-area-to-volume ratios is 6 $cm^2/g$ lipid to 1000 $cm^2/g$ lipid. The larger surface area configurations permit greater total organic contaminant flux into the enclosed model lipid or into a reactant media per unit of time, which increases airborne contaminant removal rates and reduces the time required to saturate the device. Configurations with large surface areas or surface-area-to-volume ratios (greater than 100 $cm^2/g$ lipid) are particularly useful for applications in which the time required to remove contaminant residues (e.g. greater than a 90% reduction) is an important factor. For some large scale remediation applications, adequate rates of contaminant removal from a variety of atmospheric situations can be achieved by employing a number of devices having high surface area configurations.

According to one embodiment, approximately 50 g of animal fat, plant oil or a mixture thereof is placed in a 3 meter length of 15 centimeter wide lay flat, low density polyethylene tubing having a wall thickness of 0.005 or 0.013 centimeters. The liquid is subsequently spread down the length of the tubing. Afterwards, the resulting 3 meter long, high surface-area-to-volume ribbon tubing is sealed with clamps or heat sealed, and placed in a test atmosphere. The enclosed lipid tubing configured as above can be used in multiple single arrays or cluster arrays. By using many of these lipid-containing enclosures, contaminated air can be exposed to a large surface area for adequate removal rates of organic compounds from the vapor phase.

The capacity of the device for removing a contaminant is determined by its lipid volume and by the contaminant's steady state distribution coefficient between the vapor phase in the ambient environment and the selected sequestration phase. For example, after 28 days, PCBs were concentrated $1.63\times10^5$ times higher in polyethylene enclosed triolein than in the surrounding air. The ultrathin film of smaller molecular weight lipid on the surface of the polyethylene tubing was determined to have a concentration factor of $9.75\times10^5$ which is six fold higher than that of the triolein inside the device. This shows that the ultrathin lipid component layer functions as a high efficiency trap for airborne organics in the vapor phase.

It has been determined that, using the device of the present invention, 1 Kg of lipid could remove, at a minimum, 6.9 mg of PCBs. Thus, $1.37\times10^5$ $m^3$ of air containing 50 $ng/m^3$ of PCBs could be purified by 1 Kg of similar lipid enclosed in polyethylene film. This does not include the contribution of the ultrathin exterior lipid layer. Low surface-area-to-volume configurations (less than 100 $cm^2/g$ lipid) may be more applicable to some long-term atmospheric cleanups because of their large capacity.

Using configurations with high surface-area-to-volume ratios, significant portions of contaminant residues recovered from atmospheric exposure, are usually found in the polymer matrix. This is due to the fact that the mass of the polymer exceeds the mass of the lipid. Similar designs employing extractive reaction media, various thin film layer media (e.g., oils, fats, surfactants, organic acids, bases, silicone fluids, etc.), time released configurations, enclosed solid phase adsorbents, etc. can also be used.

As discussed above, molecular size and polarity are major contaminant-related factors that limit the transport or uptake rate of an organic compound through nonporous polymers. For most configurations of the present invention, the upper size limit of organic vapor molecules that will be sequestered, appears to approximate that of mirex (546 mw), as its diffusion rate through polyethylene is very slow. Organic compounds having a molecular weight below approximately 600 may still have unacceptably low transport rates through nonpolar polymeric films if they have polar functional groups. For example, the permeability of small molecular weight organics through polyethylene (constant temperature and pressure) decreases according to functional groups as follows: halogenated hydrocarbons, hydrocarbons, ethers, esters, ketones, aldehydes, nitro-derivatives, acids and alcohols. This type of resistance to mass transport or diffusion reduces the usefulness of very nonpolar polymers like polyethylene, polypropylene and Silastic® for applications dealing with polar phenols, alcohols, and organic acid contaminants.

However, use of nonpolar polymers to enclose lipid media is applicable to the sequestration of many nonpolar and moderately polar polyaromatic hydrocarbons, aliphatic hydrocarbons, organochlorines, including industrial contaminants such as PCBs, dioxins and halocarbons, as well as insecticides such as DDT and chlordane, and other pesticides. For more polar organic contaminants, use of a polar polymer such as a polyimide, polyethylene terphthlate or polycarbonate is preferred in order to achieve adequate transport rates through the polymer matrix. Ideally, synthetic polymers can be selected that have a high affinity for the contaminant chemical classes of concern without significant polymer-contaminant interaction that could limit contaminant uptake of the device.

Temperature and pressure also affect the diffusion rates of contaminants (organic vapors) through nonporous polymeric films. Synoptically, increased temperature will generally result in increased transport rates of a contaminant through a particular polymeric film. Increased atmospheric pressure generally results in an increase in an organic compound's permeability. The physical properties of the membrane material should be taken into consideration for applications in extreme temperatures and/or pressure. For example, polyethylene can be used at very high pressures, but the desired thin film configurations can only be used with small pressure differentials across the membrane. Otherwise, the membrane needs to be fully supported by laminating the nonporous membrane to a thicker microporous membrane as discussed above.

The types of lipids or other sequestration media suitable for a variety of applications of the device are an important consideration in establishing the range of operating conditions. The choices of model lipid for use in the present invention depends on the application. Although not essential, model lipids should be liquids within the temperature range of specific applications, due to much slower transport in solid phases (increased times required for contaminant uptake). Mixed triglycerides from fish oil, peanut oil, soybean oil, etc. are a preferred choice of inexpensive model lipids. The addition of an antioxidant may be necessary for some extended applications, because unsaturated lipids that are liquids at 30° C. or less are somewhat unstable due to the potential for oxidation at unsaturated sites on the esterified fatty acid molecules. Also, many synthetic large molecular weight hydrocarbons or silicones may serve as acceptable sequestration media for concentrating nonpolar, vapor phase organic contaminants. For more polar contaminants such as certain herbicides, organophosphate insecticides, mycotoxins, and industrial chemicals, the use of more polar biomembrane-associated model lipids may be necessary for optimum recovery of these contaminants. A suitable model for more polar lipids is lecithin, a common large molecular weight phospholipid. Obviously many large molecular weight synthetic, organic compounds may also serve as a sequestration media for more polar contaminants. Extractive reaction media are situation specific, but are easily constructed using combinations of either nonpolar or polar polymeric membranes and appropriate enclosed solutions or solid phases. For volatile or organic contaminants with high vapor pressures, the addition of small amount of trapping media, e.g. charcoal, to the lipid will enhance retention of these analytes. Also, lipid soluble stable antibodies may be added to the sequestration media to retain specific types of analytes (haptens).

An alternate configuration for the device of the present invention can include small diameter, relatively thin-walled polymeric tubing (wall thickness of about 0.001 cm) arranged in bundles similar to the hollow fibers used for conventional ultrafiltration, and filled with lipid or other appropriate sequestration media. The bundle ends can be connected to a loop of 0.32 cm Teflon tubing with an in-line column of gas-phase charcoal such as coconut charcoal and a peristaltic pump. Then the tubing bundles are placed in contaminated atmospheres and as residues are accumulated in tubing-enclosed lipids, they are removed by sorption on charcoal, as the lipid is slowly circulated through the loop. Because the charcoal removes contaminants from the sequestration media, equilibrium is not reached, resulting in greater long term removal rates of atmospheric contaminants and in an increased capacity of this configuration for most contaminants. In this case ultimate removal is controlled by charcoal adsorption. Configurations using other adsorbent or reactive media can also be used.

The device of the present invention, although relatively simple, embodies attributes that mimic the respiratory uptake of organic compounds by the lungs. The device's ultrathin layer serves not only to concentrate organic compounds from the vapor phase, but also functions to entrap some airborne particulate matter, analogous to entrainment of particulate matter in the lungs. No other organic vapor monitors mimic respiratory uptake. Therefore, the present invention provides a better estimate of occupational airborne contaminant exposure than known devices. In addition the present invention provides high sampling rates even though it is an inexpensive, passive device.

The device of the present invention has been demonstrated to be both highly efficient and effective for concentrating organic compounds from the atmosphere. A very small 1 g configuration of the device has been determined to sample approximately 6 $m^3$ of air per day for PCBs in the vapor state in a passive mode. This sampling rate corresponds to 6000 L per day and is comparable to sampling rates employed in large scale active sampling systems.

Although the invention has been described with reference to particular means, materials and embodiments, from the foregoing description, one skilled in the art can easily ascertain the essential characteristics of the present invention and various changes and modifications may be made to adopt the various uses and conditions thereof without departing from the spirit and scope of the present invention as described by the claims which follow.

What is claimed is:

1. A method for collecting organic compounds from an atmosphere which comprises:
   providing an envelope made from a nonporous membrane which includes an inner space, an exterior surface, and membrane transport corridors that communicate between said inner space and said exterior surface;
   providing an organic compound collection media within said inner space, said organic compound collection media comprises a first component having a molecular weight which is too large to pass through said membrane transport corridors and a second component having a molecular weight which is sufficiently small so as to pass through said membrane transport corridors;
   allowing a portion of said second component to diffuse through said transport corridors and form a film on said exterior surface of said nonporous membrane envelope; and
   exposing said envelope to an atmosphere which contains organic compounds, whereby during said exposure organic compounds are absorbed by said exterior film of said second component and transferred into said inner space of said envelope so as to be collected therein.

2. A method for collecting organic compounds from an atmosphere according to claim 1, wherein said atmosphere is within a confined space and said method further involves reducing the level of organic compounds within said confined space.

3. A method for collecting organic compounds from an atmosphere according to claim 2, wherein said confined space comprises a building.

4. A method for collecting organic compounds from an atmosphere according to claim 1, wherein organic compounds collected in said inner space of said envelope are subsequently analyzed.

5. A method for collecting organic compounds from an atmosphere according to claim 1, further comprising supporting said nonporous membrane on a microporous support membrane.

6. A method for collecting organic compounds from an atmosphere according to claim 1, wherein said nonporous membrane is made from a member selected from the group consisting of polyethylene, polyethylene terphthalate, polyimide, polypropylene, polyvinyl chloride, silicone, and mixtures thereof.

7. A method for collecting organic compounds from an atmosphere according to claim 1, wherein said collection media comprises a lipid, oil, silicone, hydrocarbon, or other lipid-like fluids.

8. A method for collecting organic compounds from an atmosphere according to claim 1, wherein said envelope has a surface-area-to-volume ratio of 6 $cm^2/g$ to 1000 $cm^2/g$.

9. A method for collecting organic compounds from an atmosphere according to claim 1, wherein said collection media is reactive to organic compounds which are collected.

10. A device for collecting organic compounds from an atmosphere which comprises:
- an envelope made from a nonporous membrane which includes an inner space, an exterior surface, and membrane transport corridors which provide pathways for exchange between said inner space and said exterior surface; and
- an organic compound collection media within said inner space, said organic compound collection media comprising a first component having a molecular weight which is too large to pass through said membrane transport corridors and a second component having a molecular weight which is sufficiently small so as to pass through said membrane transport corridors,
- whereby a portion of said second component forms a film on said exterior surface of said nonporous membrane envelope and said first component is contained within said inner space of said envelope, and organic compounds are absorbed by said exterior film of said second component and are transported through said membrane transport corridors into said inner space of said envelope.

11. A device for collecting organic compounds from an atmosphere according to claim 10, wherein said nonporous membrane is made from a member selected from the group consisting of polyethylene, polypropylene, polyvinyl chloride, silicone, polyethylene terphthalate, polyimide, and mixtures thereof.

12. A device for collecting organic compounds from an atmosphere according to claim 10, wherein said nonporous membrane is laminated to a microporous support membrane.

13. A device for collecting organic compounds from an atmosphere according to claim 10, wherein said nonporous membrane has a thickness of 5 to 500 $\mu$m.

14. A device for collecting organic compounds from an atmosphere according to claim 10, wherein the surface-area-to-volume ratio of said device is 6 $cm^2/g$ to 1000 $cm^2/g$ collection media.

15. A device for collecting organic compounds from an atmosphere according to claim 10, wherein said collection media comprises a lipid or an oil.

16. A device for collecting organic compounds from an atmosphere according to claim 15, wherein said collection media comprises triolein.

17. A device for collecting organic compounds from an atmosphere according to claim 10, wherein said collection media is reactive to organic compounds which are collected.

18. A device for collecting organic compounds from an atmosphere according to claim 17, wherein said collection media is a member selected from the group consisting of organic acids, organic bases, silicone, hydrocarbons, and other lipid-like fluids, and mixtures thereof.

* * * * *

UNITED STATES PATENT AND TRADEMARK OFFICE
CERTIFICATE OF CORRECTION

PATENT NO. : 5,395,426
DATED : March 7, 1995
INVENTOR(S) : James N. HUCKINS et al It is certified that error appears in the above-indentified patent and that said Letters Patent is hereby corrected as shown below:

Item [75] should read as follows:

--[75] Inventors: James N. Huckins; Jimmie D. Petty; James L. Zajicek; Virginia L. Gibson, all of Columbia, Mo.--

Signed and Sealed this

Twelfth Day of March, 1996

Attest:

BRUCE LEHMAN

Attesting Officer

Commissioner of Patents and Trademarks